United States Patent
Liu et al.

(10) Patent No.: US 9,373,268 B2
(45) Date of Patent: Jun. 21, 2016

(54) SPEECH AID SYSTEM

(71) Applicants: Ching-Feng Liu, Kaohsiung (TW); Hsiao-Han Chen, Tainan (TW)

(72) Inventors: Ching-Feng Liu, Kaohsiung (TW); Hsiao-Han Chen, Tainan (TW)

(*) Notice: Subject to any disclaimer, the term of this patent is extended or adjusted under 35 U.S.C. 154(b) by 266 days.

(21) Appl. No.: 14/294,994

(22) Filed: Jun. 3, 2014

(65) Prior Publication Data

US 2014/0358551 A1 Dec. 4, 2014

(30) Foreign Application Priority Data

Jun. 4, 2013 (TW) .............................. 102119780 A
Jan. 16, 2014 (TW) .............................. 103101604 A

(51) Int. Cl.
*G09B 21/00* (2006.01)
*A61F 2/20* (2006.01)
*A61M 16/04* (2006.01)
*G10K 11/22* (2006.01)

(52) U.S. Cl.
CPC . *G09B 21/00* (2013.01); *A61F 2/20* (2013.01); *A61M 16/0468* (2013.01); *A61F 2002/206* (2013.01); *A61M 2205/3331* (2013.01); *A61M 2205/3358* (2013.01); *A61M 2205/3375* (2013.01); *A61M 2205/3569* (2013.01); *A61M 2205/3592* (2013.01); *A61M 2205/7545* (2013.01); *A61M 2209/01* (2013.01); *A61M 2209/088* (2013.01); *G10K 11/22* (2013.01)

(58) Field of Classification Search
CPC ... A61F 2/20; G10L 13/04; G10L 2021/0575; G10L 21/02; G10L 21/0364; A61H 2201/165; A61H 2201/5058; A61H 2205/04
USPC ................ 705/17; 704/271, 261, 235; 623/9; 600/23; 392/70; 128/204.23
See application file for complete search history.

(56) References Cited

U.S. PATENT DOCUMENTS

| | | | | | |
|---|---|---|---|---|---|
| 4,550,427 | A | * | 10/1985 | Katz | A61F 2/20 381/70 |
| 4,586,931 | A | * | 5/1986 | Blom | A61F 4/00 623/9 |
| 4,862,503 | A | * | 8/1989 | Rothenberg | G10L 25/48 704/235 |
| 5,326,349 | A | * | 7/1994 | Baraff | A61F 2/20 381/70 |
| 5,528,726 | A | * | 6/1996 | Cook | G10L 13/04 704/261 |
| 5,729,694 | A | * | 3/1998 | Holzrichter | G10L 15/24 704/270 |
| 6,795,807 | B1 | * | 9/2004 | Baraff | G10L 21/0208 704/248 |
| 7,676,372 | B1 | * | 3/2010 | Oba | G09B 21/009 434/169 |
| 8,449,445 | B2 | * | 5/2013 | Ludlow | A61H 23/0245 600/23 |
| 2004/0024455 | A1 | * | 2/2004 | de Vries | A61F 2/203 623/9 |
| 2005/0178385 | A1 | * | 8/2005 | Dellaca' | A61B 5/085 128/204.23 |

* cited by examiner

*Primary Examiner* — Michael Colucci
(74) *Attorney, Agent, or Firm* — Muncy, Geissler, Olds & Lowe, P.C.

(57) ABSTRACT

A speech aid system includes a tube for mounting at a tracheostomy of a user, a voice parameter acquiring device mounted to the tube and generating a voice parameter signal according to airflow applied within the tube resulting from attempt by the user to speak, a processor generating an audio signal corresponding to the voice parameter signal, and a sound generator for mounting in an oral cavity of the user. The sound generator produces a substitute glottal sound corresponding to the audio signal.

24 Claims, 10 Drawing Sheets

9,373,268 B2

SPEECH AID SYSTEM

CROSS-REFERENCE TO RELATED APPLICATION

This application claims priority to Taiwanese Application Nos. 102119780 and 103101604, filed respectively on Jun. 4, 2013 and Jan. 16, 2014.

BACKGROUND OF THE INVENTION

1. Field of the Invention

The invention relates to a speech aid system adapted for use by a tracheostomized patient.

2. Description of the Related Art

Vowels of human languages are produced by: generating a glottal sound by vibration of the glottis as a result of air from the respiratory subsystem, and using the tongue, the lips and the soft palate to construct a vocal tract with a shape according to a sound that is to be produced. However, a laryngectomized patient whose larynx is removed and whose windpipe is tracheostomized to be connected to the neck is unable to produce a glottal sound for speech.

U.S. Pat. No. 4,550,427 discloses a conventional artificial larynx having an intraoral speaker for use by a laryngectomized patient. However, volume variation in a spoken sentence is unable to be controlled as desired by the user, so that the voice produced by such a conventional artificial larynx would be somewhat unnatural.

SUMMARY OF THE INVENTION

Therefore, an object of the present invention is to provide a speech aid system that may alleviate the above drawback of the prior art.

According to the present invention, a speech aid system comprises: a tube configured for mounting at a tracheostomy of a user; a voice parameter acquiring device mounted to the tube, and configured to sense airflow applied within the tube resulting from attempt by the user to speak, and to generate a voice parameter signal according to the airflow sensed thereby; a processor configured to receive the voice parameter signal from the voice parameter acquiring device, and to generate an audio signal corresponding to the voice parameter signal; and a sound generator configured for mounting in an oral cavity of the user, configured to receive the audio signal from the processor, and configured to produce a substitute glottal sound corresponding to the audio signal.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
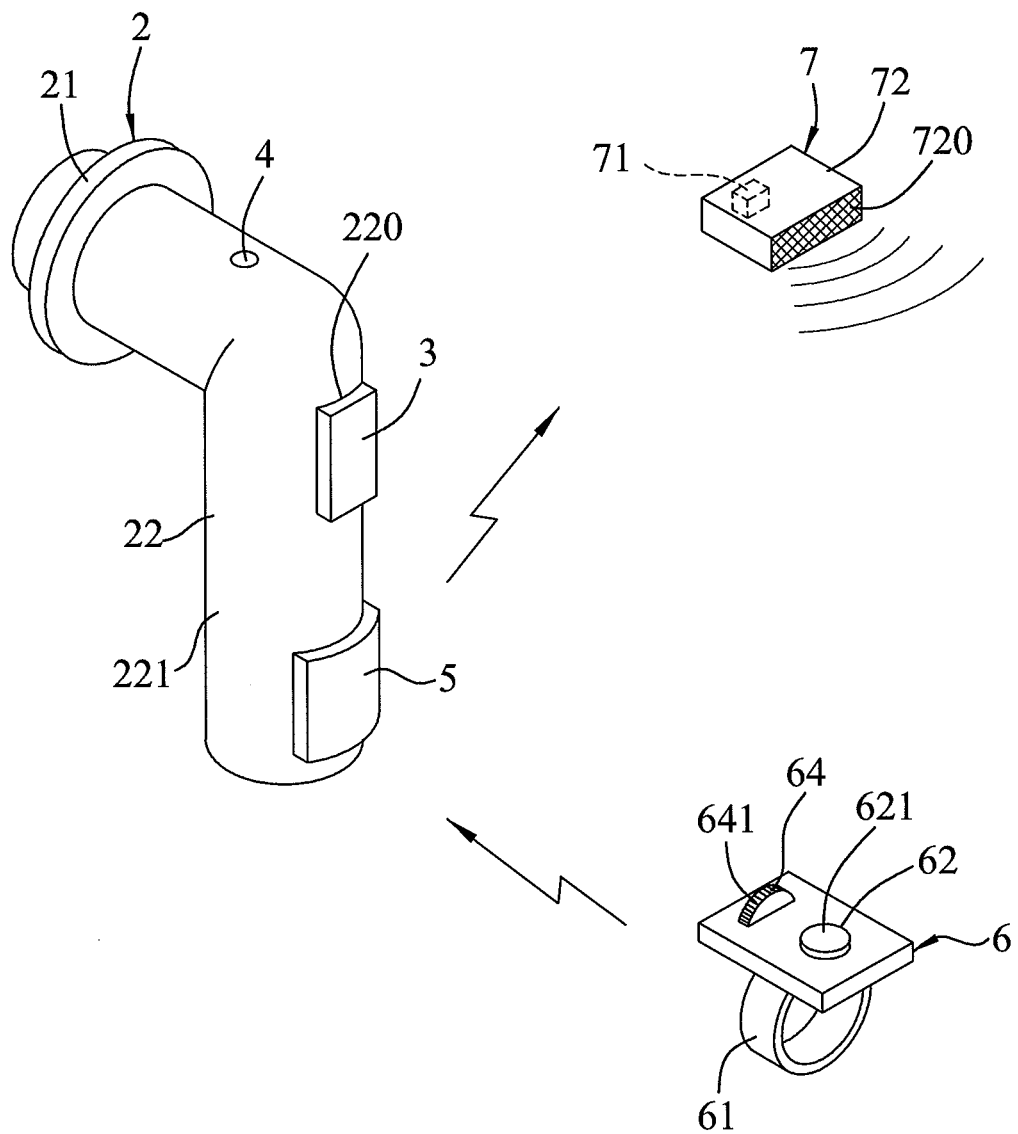
FIG. 1 is a perspective diagram showing a first preferred embodiment of the speech aid system according to the present invention.
Figure 2:
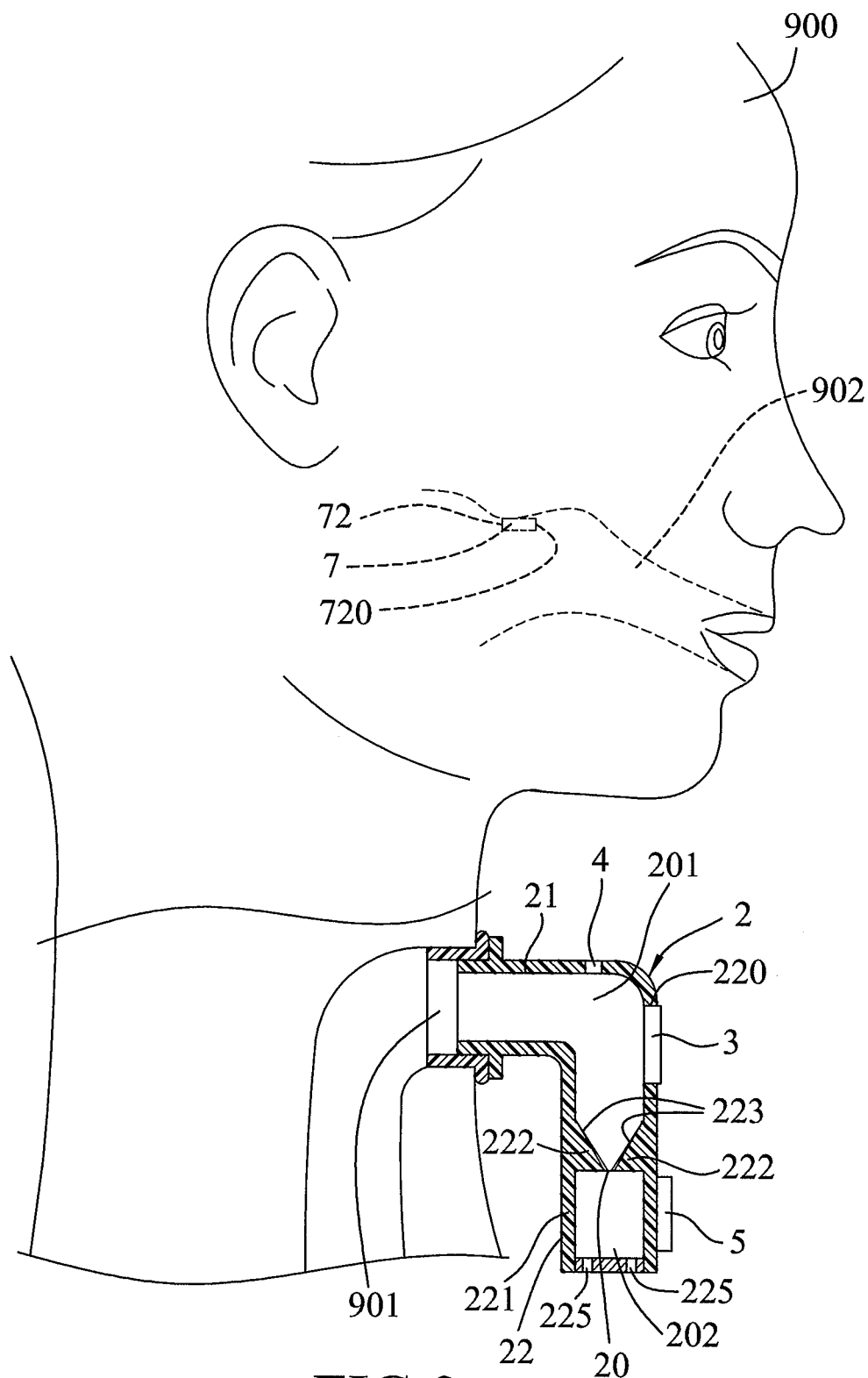
FIG. 2 is a side sectional view illustrating the first preferred embodiment in a state of use.

Referring to FIGS. 1 and 2, the first preferred embodiment of the speech aid system according to this invention is shown to be used by a user 900 who may be a patient whose larynx was removed.

The speech aid system includes a tube 2 for mounting at a tracheostomy 901 of the user 900, a gate 3, a voice parameter acquiring device 4, and a processor 5 that are mounted to the tube 2, a remote controller 6 to be worn by the user 900, and a sound generator 7 configured for mounting in an oral cavity 902 of the user 900.

Figure 3:
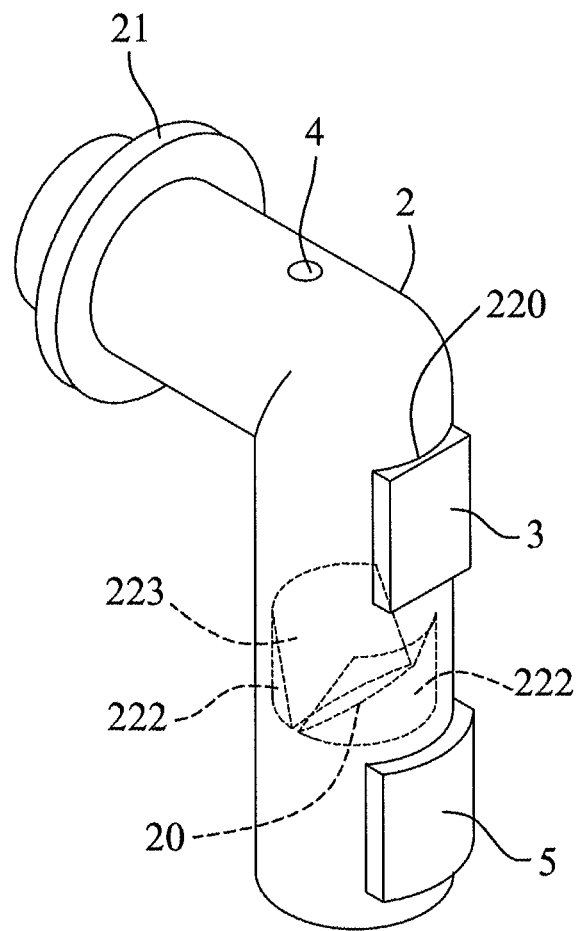
FIG. 3 is a perspective view showing a tube of the first preferred embodiment.
Figure 4:
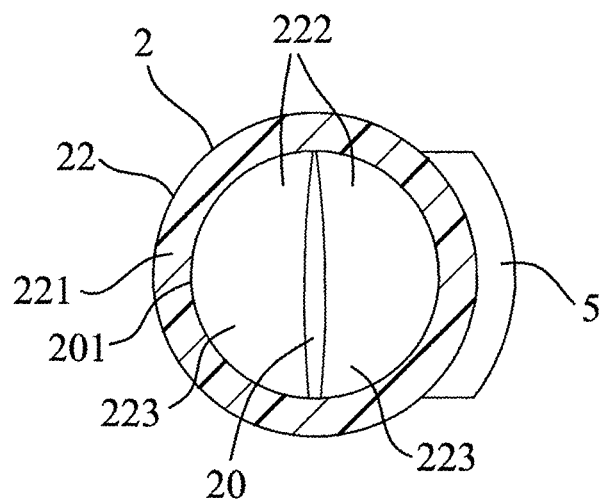
FIG. 4 is a cross-sectional view of the tube of the first preferred embodiment.

As shown in FIGS. 2 to 4, the tube 2 is configured to imitate the action of the glottis during speaking, and has a connecting section 21 for mounting at the tracheostomy 901 of the user 900, and an artificial glottis section 22 connected to the connecting section 21. An internal space of the connection section 21 spatially communicates with the tracheostomy 901. The artificial glottis section 22 bends downward and has a tubular portion 221 that extends in an up-down direction, and that has vent holes 225 for spatial communication with the external environment, and two spaced-apart protrusions 222 that protrude radially and inwardly from an inner peripheral surface of the tubular portion 221 and that form an artificial glottis 20 extending along an axial direction of the tubular portion 221, so that a first space 201 and a second space 202 are formed at opposite sides of the artificial glottis 20 within the tubular portion 221. The first space 201 is in spatial communication with the internal space of the connecting section 21, and the second space 202 is in spatial communication with the external environment via the vent holes 225. The tubular portion 221 is formed with a breathing hole 220 that extends through a tube wall thereof and that spatially communicates with the first space 201.

Each of the protrusions 222 has an airflow guiding surface 223. The airflow guiding surfaces 223 extend slantingly, downwardly, and toward each other, and cooperate with the inner peripheral surface of the tubular portion 221 to form the artificial glottis 20. In this embodiment, the artificial glottis 20 has a radial size that is gradually reduced in a direction from the first space 201 to the second space 202, and has a shape of a slit (see FIG. 4) extending in a radial direction of the tubular portion 221 for simulating action of a glottis during normal speaking.

In this embodiment, the gate 3 is an electronic air valve fixedly mounted in the breathing hole 220 and controlled by the processor 5 to open and close the breathing hole 220. When the breathing hole 220 is opened, the first space 201 spatially communicates with the external environment so that the user 900 may breathe using the tube 2. When the user 900 attempts to speak, the gate 3 may be controlled by the processor 5 to close the breathing hole 220, so that the air entering the tube 2 passes through the artificial glottis 20 and is exhausted via the vent holes 225.

The voice parameter acquiring device 4 senses airflow sourced from the tracheostomy 901 and applied within the tube 2 resulting from attempt by the user 900 to speak, and generates a voice parameter signal that is provided to the processor 5 according to the airflow sensed thereby. In this embodiment, the voice parameter acquiring device 4 is a pressure sensor mounted to the tubular portion 221 and exposed to the first space 201. The pressure sensor generates the voice parameter signal according to a difference between air pressure in the first space 201 and ambient air pressure.

Figure 5:
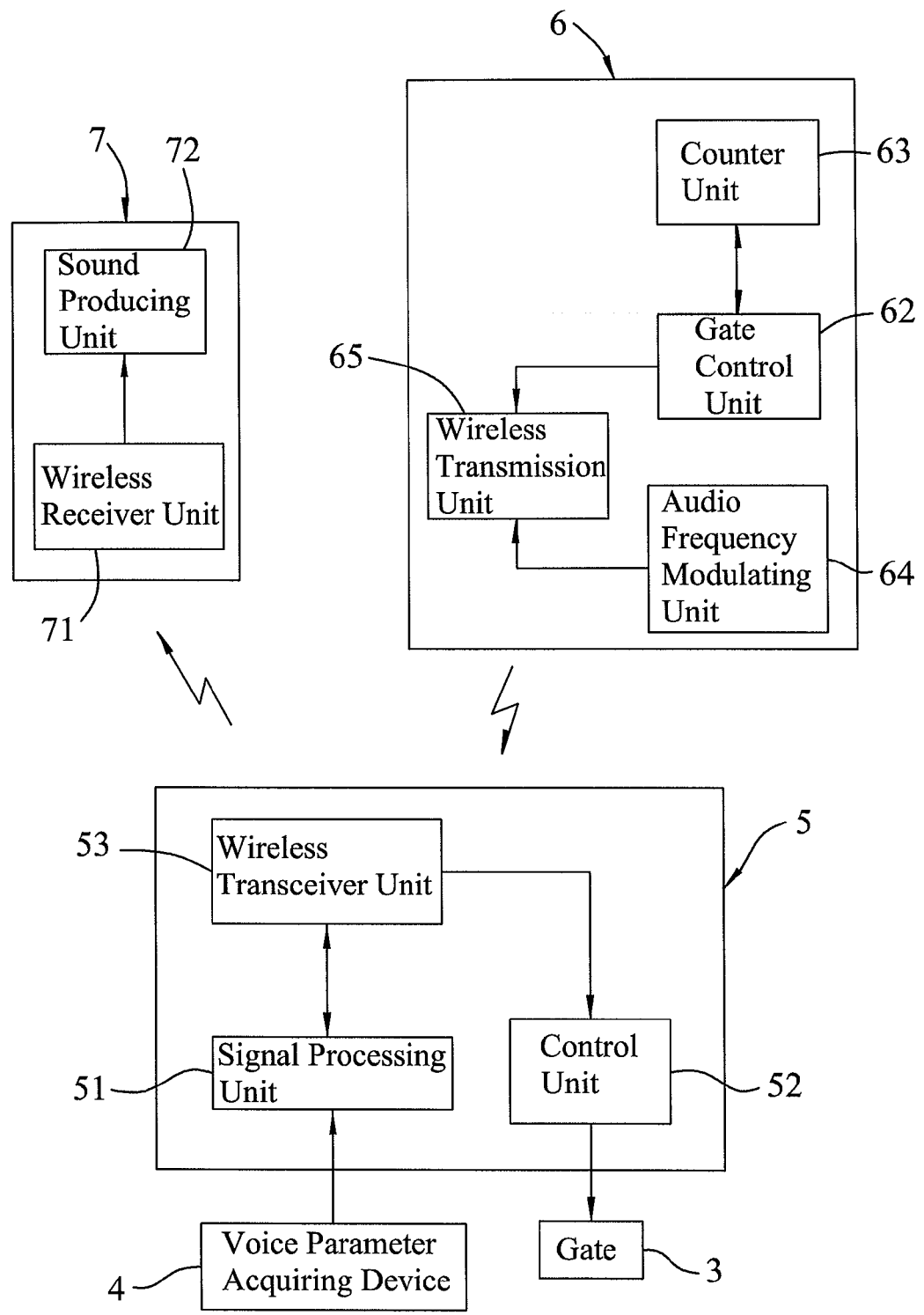
FIG. 5 is a block diagram of the first preferred embodiment.

Referring to FIGS. 2, 3 and 5, the processor 5 is mounted to an outer peripheral surface of the tubular portion 221, and includes a signal processing unit 51 electrically coupled to the voice parameter acquiring device 4, a control unit 52 that is configured to control opening and closing actions of the gate 3, and a wireless transceiver unit 53 that is configured to wirelessly receive a gate control signal and a frequency modulation signal from the remote controller 6, and to wirelessly communicate with the sound generator 7. The gate control signal may be a gate opening signal or a gate closing signal.

The signal processing unit 51 is configured to start sensing of the voice parameter acquiring device 4 in response to the gate closing signal, and to stop sensing of the voice parameter acquiring device 4 in response to the gate opening signal. The signal processing unit 51 may be configured to process the voice parameter signal using pre-filtering, analog-to-digital conversion, time-based analysis of variation of pressure difference, etc. Since the volume of speech is proportional to the pressure difference to be sensed by the voice parameter acquiring device 4, and the time length of speech and the time points of the pauses are associated with the length of time for which the pressure within the first space 201 is sustained, and the time intervals among the pressure waves of the airflow that passes through the artificial glottis 20, the signal processing unit 51 is able to convert the voice parameter signal into an audio signal associated with the volume of the speech according to the voice parameter signal received at different time points, so as to imitate a glottal sound produced by the vocal cord resulting from passage of the air flowing through the glottis. In this embodiment, the signal processing unit 51 is further configured to modulate an audio frequency parameter of the audio signal according to the frequency modulation signal received by the wireless transceiver unit 53, and to wirelessly transmit to the sound generator 7 the audio signal having the modulated audio frequency parameter through the wireless transceiver unit 53.

In practice, the signal processing unit 51 may be further configured to set a transmission time point at which the wireless transceiver unit 53 transmits the audio signal. That is, the transmission time point may be set according to the mouth-shaping time at which the user 900 configures the mouth shape, such that the sound generator 7 produces the substitute glottal sound at the time approximately matching the mouth-shaping time, and the user 900 may speak more precisely.

The control unit 52 is configured to control the gate 3 to open the breathing hole 220 in response to the gate opening signal received by the wireless transceiver unit 53, and to control the gate 3 to close the breathing hole 220 in response to the gate closing signal received by the wireless transceiver unit 53.

In this embodiment, the processor 5, the gate 3 and the voice parameter acquiring device 4 communicate with each other using signal wires (not shown). The signal wires may be hidden in the artificial glottis section 22, or may be exposed from the outer peripheral surface of the tubular portion 221. In other embodiments, communication thereamong may be wireless. Since various techniques are applicable for communication among the processor 5, the gate 3 and the voice parameter acquiring device 4, and since such techniques are not characterizing features of this invention, further details thereof will be omitted herein for the sake of brevity.

Further referring to FIG. 1, the remote controller 6 includes a holder 61 to be worn by the user 900, a gate control unit 62 operable to generate a gate control signal, a counter unit 63 (see FIG. 5), an audio frequency modulating unit 64, and a wireless transmission unit 65 (see FIG. 5). In this embodiment, the holder 61 is configured as a ring to be worn on a user's finger. In other embodiments, the holder 61 may be configured as a bracelet, a collar, etc.

The gate control unit 62 includes a control button 621 exposed from a surface of the holder 61. In this embodiment, when the control button 621 is pressed, the gate control unit 62 correspondingly generates the gate closing signal. At the same time, the counter unit 63 starts to count for a predetermined time period. When the predetermined time period has elapsed, the gate control unit 62 correspondingly generates the gate opening signal. The audio frequency modulating unit 64 includes an adjusting component 641 exposed from the surface of the holder 61. When the adjusting component 641 is operated, the audio frequency modulating unit 64 correspondingly generates the frequency modulation signal that is provided to the processor 5. The wireless transmission unit 65 is configured to wirelessly transmit the gate closing signal, the gate opening signal and the frequency modulation signal.

In this embodiment, the control button 621 and the adjusting component 641 are a physical button and a physical rotary knob, respectively. In other embodiments, implementations thereof may employ a touch screen for ensuring flatness of the surface of the holder 61.

The sound generator 7 includes a wireless receiver unit 71 and a sound producing unit 72 electrically coupled to the wireless receiver unit 71. The wireless receiver unit 71 is configured to wirelessly receive the audio signal from the processor 5. The sound producing unit 72 has a sound output surface 720 extending horizontally and facing an opening of the user's mouth, and is configured to produce, in response to the audio signal received by the wireless receiver unit 71, the substitute glottal sound in a form of a linear wave. The substitute glottal sound is provided into the oral cavity 902, so that the user 900 may speak like an ordinary person via articulation using the mouth, the tongue, and the palate.

In practice, the tube 2 is mounted at the tracheostomy 901 of the user 900, the sound generator 7 is mounted in the oral cavity 902, and the remote controller 6 is worn on the hand of the user 900. By virtue of structural designs of the first space 201, the second space 202 and the artificial glottis 20, structures of a larynx and a glottis of an ordinary person under speaking may be simulated for aiding speech of the user 900.

In a common state, the breathing hole 220 is opened by the gate 3 to facilitate breathing of the user 900 through the tube 2. When the user 900 attempts to speak, the control button 621 may be pressed once such that the processor 5 controls the gate 3 to close the breathing hole 220 for the predetermined time period. At the same time, the audio frequency modulating unit 64 is driven to generate the frequency modulation signal, and the processor 5 continuously receives and processes the voice parameter signal from the voice parameter acquiring unit 4, and continuously transmits the audio signal to the sound generator 7 using a specific transmission frequency.

When the breathing hole 220 is closed by the gate 3, the user 900 may speak in an ordinary manner. At the same time, the lungs of the user 900 compress air so that a high air pressure is generated within the tube 2. The air is compressed to flow through the artificial glottis 20, and is exhausted from the tube 2 through the vent holes 225 that spatially communicate with the second space 202. The voice parameter acquiring device 4 continuously compares the air pressure in the first space 201 with the ambient air pressure, and continuously outputs the voice parameter signal according to the difference between the air pressures. The processor 5 receives and processes the voice parameter signal according to the frequency modulation signal, so as to generate the audio signal that is transmitted to the sound generator 7 for driving the sound generator 7 to produce the substitute glottal sound.

Since the time elapsed between obtaining of the voice parameter signal and production of the substitute glottal sound is very short, and the time at which the substitute glottal sound is produced may be set by the user 900, the time at which the substitute glottal sound is produced and the mouth-shaping time may be approximately synchronized, so that the user 900 may configure the substitute glottal sound into desired spoken sound with ordinary breathing and the ordinary mouth shape. When the user 900 attempts to speak loudly, a relatively large amount of air is compressed by the lungs, resulting in a relatively large difference between the air pressures inside and outside the tube 2, which is to be sensed by the voice parameter acquiring device 4. When the user 900 attempts to speak gently, a relatively small amount of air is compressed by the lungs, resulting in a relatively small difference between the air pressures inside and outside the tube 2, which is to be sensed by the voice parameter acquiring device 4. Therefore, the audio signal generated by the processor 5 would have an amplitude that varies correspondingly, resulting in the volume variation of the substitute glottal sound. As a result, speech of the user 900 may have desired volume variation. Similarly, the lengths of the spoken sentences and the pauses among the spoken sentences may be identified by continuously sensing the difference between the air pressure in the first space 201 and the ambient air pressure, so that the sentences spoken by the user 900 may be clearly identified.

In addition, the user 900 may use the adjusting component 641 of the audio frequency modulating unit 64 to adjust the audio frequency parameter of the audio signal generated by the processor 5, so as to change an audio frequency of the substitute glottal sound produced by the sound generator 7. As a result, a desired tone, for example, a shrill voice or a deep voice, may be obtained.

When the counter unit 63 finishes counting (i.e., the predetermined time period has elapsed), the remote controller 6 transmits the gate opening signal, such that the processor 5 controls the gate 3 to open the breathing hole 220 for facilitating breathing of the user 900. The user 900 may only need to press the control button 621 again when attempting more speech.

In this embodiment, the counter unit 63 determines when the remote controller 6 should transmit the gate opening signal. In other embodiments, the counter unit 63 may be omitted, and generation of the gate opening signal may not be necessary. In one embodiment, the gate control unit 62 may be configured to continuously generate the gate closing signal only when the control button 621 is pressed, and the processor 5 may be configured to control the gate 3 to close the breathing hole 220 only when the gate closing signal is received, and to open the breathing hole 220 when otherwise. In another embodiment, the gate control unit 62 may be configured to generate the gate closing signal when the control button 621 is pressed once, and to generate the gate opening signal when the control button 621 is pressed once more, that is, the gate closing signal and the gate opening signal are generated in turns during repeated pressing of the control button 621. In yet another embodiment, the processor 5 may be further configured to count for the predetermined time period after receipt of the gate closing signal, and to control the gate 3 to open the breathing hole 220 when the predetermined time period counted by the processor 5 has elapsed, so that the opening action of the gate 3 is not necessary to be triggered by the remote controller 6.

In this embodiment, although the artificial glottis 20 has a shape of a slit extending in the radial direction of the tubular portion 221, the present invention should not be limited in this aspect. In other embodiments, the artificial glottis 20 may be formed as a circular hole or other shapes. Moreover, the tube 2 may have only one protrusion 222 to form the artificial glottis 20 alone, or to cooperate with the tubular portion 221 to form the artificial glottis 20.

Figure 6:
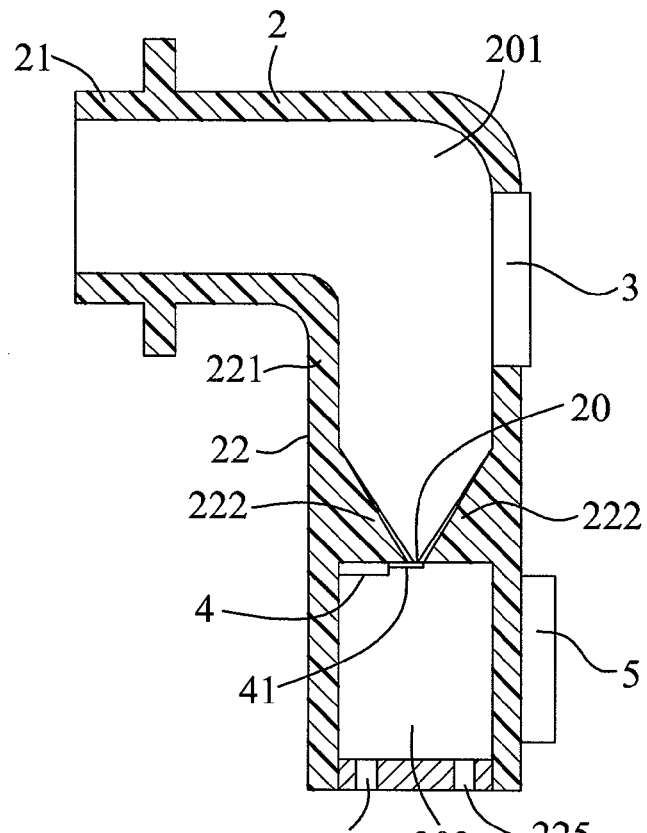
FIG. 6 is a side sectional view illustrating a tube of a second preferred embodiment of the speech aid system according to the present invention.
Figure 7:
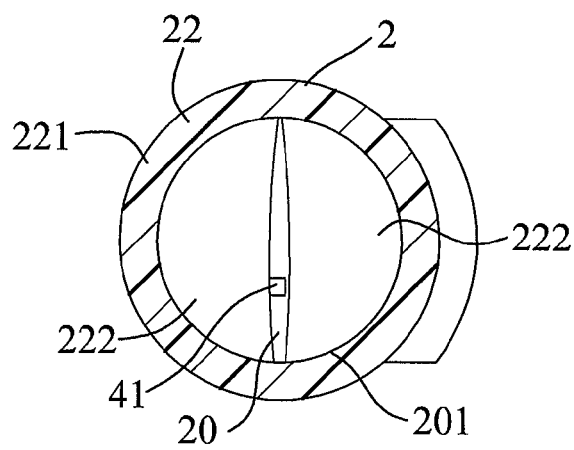
FIG. 7 is a cross-sectional view of the tube of the second preferred embodiment.

Referring to FIGS. 6 and 7, differences between the first and second preferred embodiments reside in the type and the location of the voice parameter acquiring device 4.

In the second preferred embodiment, the voice parameter acquiring device 4 is an air flow meter that is mounted to one of the protrusions 222 in the second space 202, and has a sensing portion 41 that extends horizontally so as to be visible from a top view of the artificial glottis 20, as shown in FIG. 7. The sensing portion 41 is bendable and deformable by the airflow passing through the artificial glottis 20, such that the voice parameter acquiring device 4 generates an electrical signal accordingly. Therefore, speed variation of the airflow passing through the artificial glottis 20 may be sensed for generation of a corresponding voice parameter signal. The speed of the airflow passing through the artificial glottis 20 has a positive correlation with the air pressure in the first space 201, so that the audio signal may be obtained with volume variations and the pause of the speech thus produced by the user 900 being identifiable.

Since the air flow meter is a conventional device and may be implemented in various ways, details thereof will not be described herein for the sake of brevity. In addition, the location to which the air flow meter is mounted should not be limited to the embodiment disclosed herein.

Figure 8:
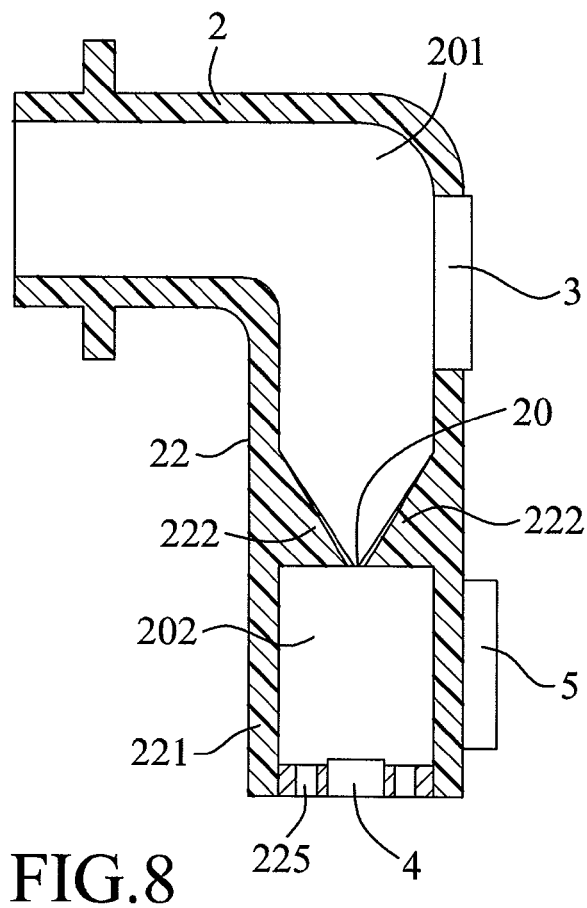
FIG. 8 is a side sectional view of a tube of a third preferred embodiment of the speech aid system according to the present invention.
Figure 9:
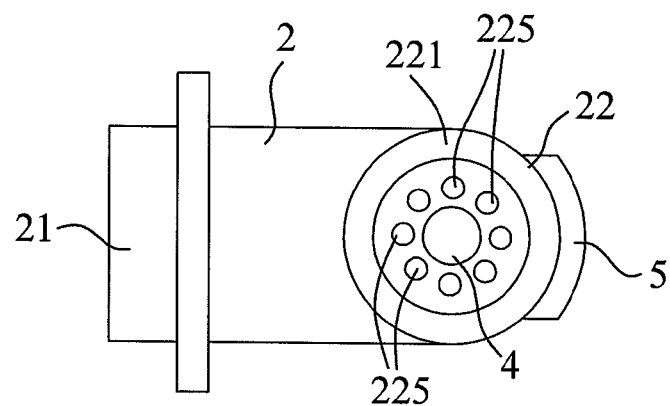
FIG. 9 is a bottom view of the tube of the third preferred embodiment.

Referring to FIGS. 8 and 9, differences between the first and third preferred embodiments reside in the configuration of the voice parameter acquiring device 4.

In the third preferred embodiment, the voice parameter acquiring device 4 is an acoustoelectric transducer (e.g., a microphone) that is mounted in the second space 202 and that generates the voice parameter signal according to amplitude of a pressure wave generated by passage of airflow through the artificial glottis 20. The amplitude of the pressure wave generated by passage of airflow through the artificial glottis 20 has a positive correlation with the air pressure in the first space 201, so that the audio signal may be obtained with the volume variation and the pause of the speech thus produced by the user 900 being identifiable.

Figure 10:
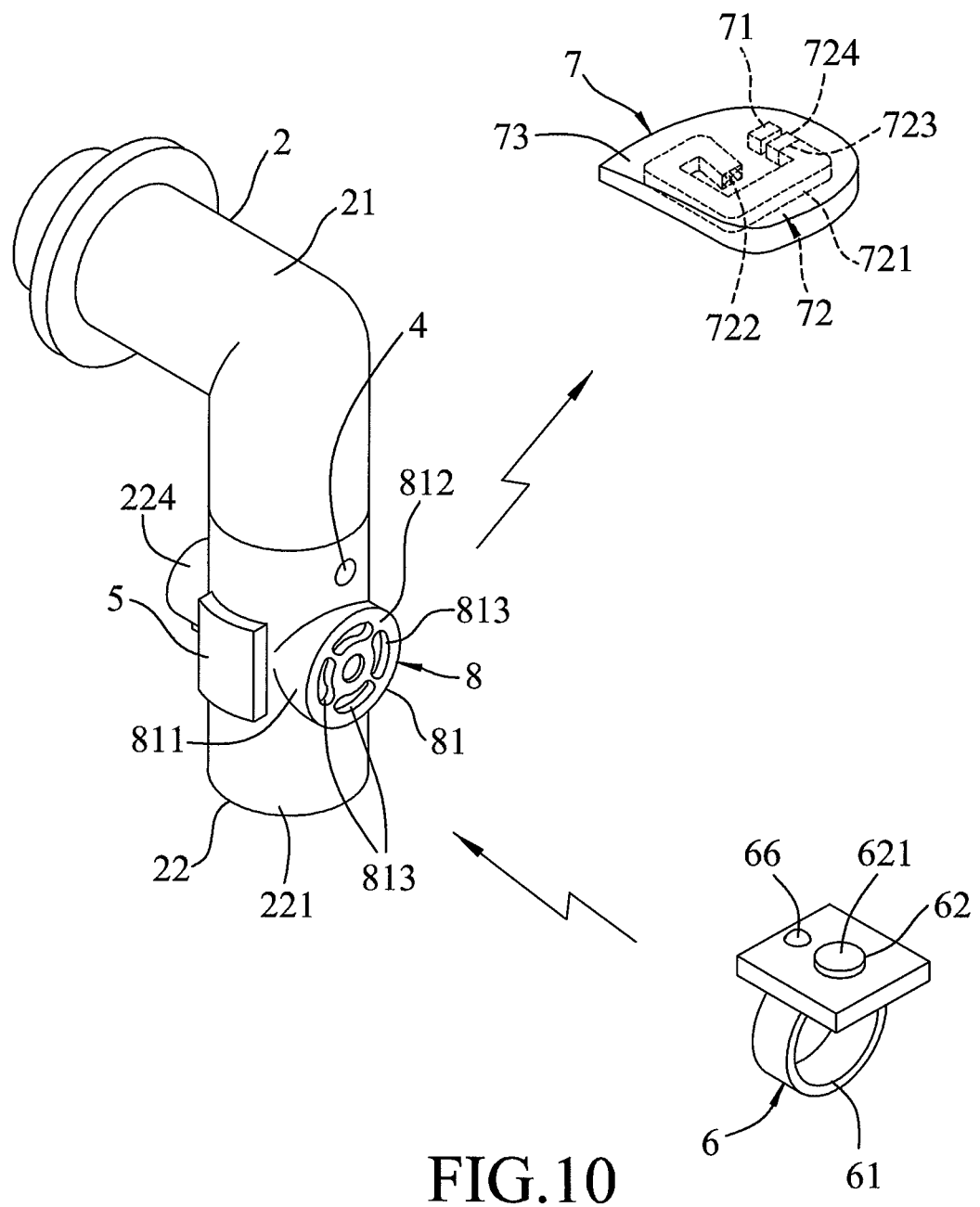
FIG. 10 is a perspective diagram showing a fourth preferred embodiment of the speech aid system according to the present invention.
Figure 11:
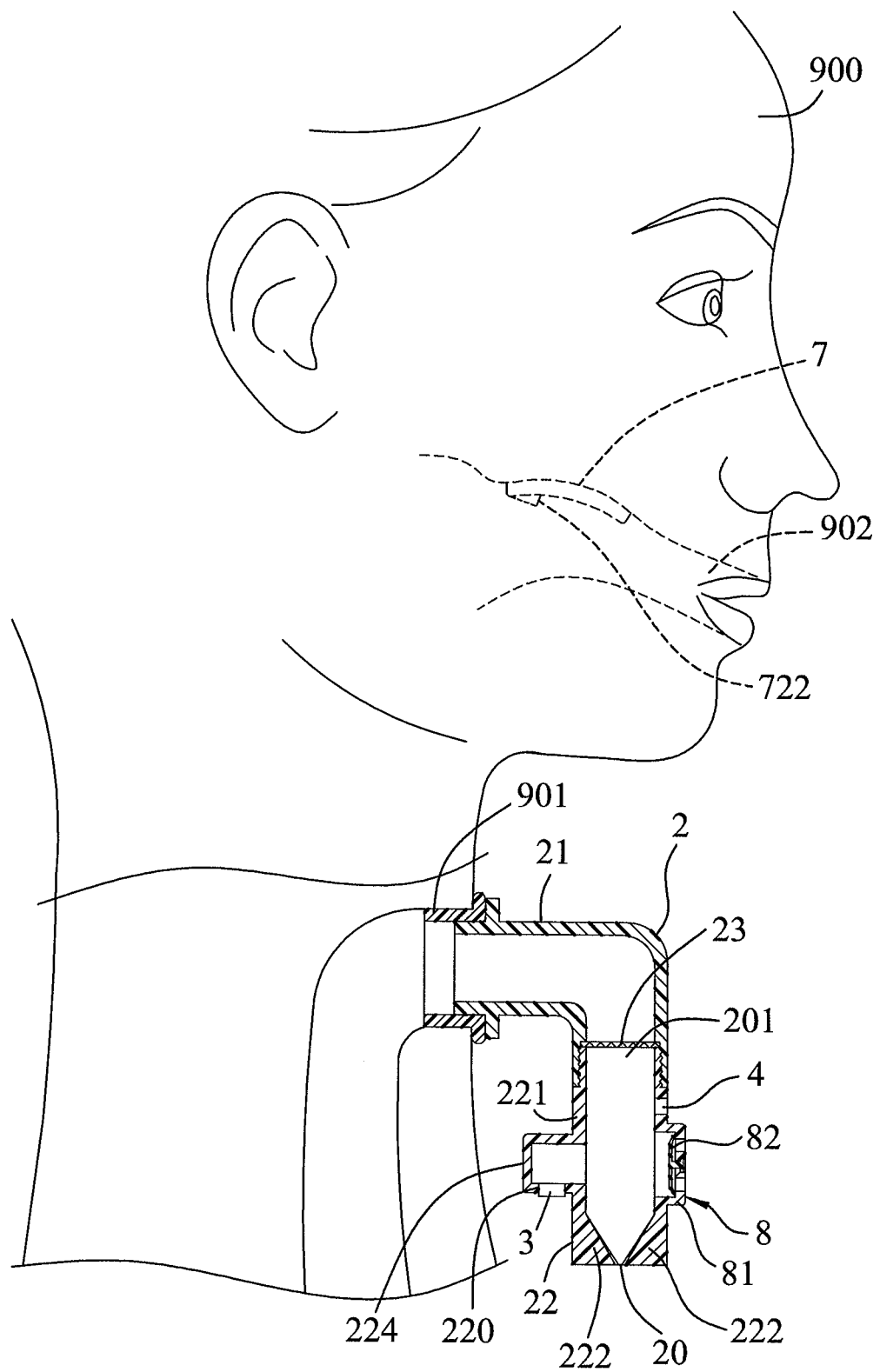
FIG. 11 is a side sectional view illustrating the fourth preferred embodiment in a state of use.
Figure 12:
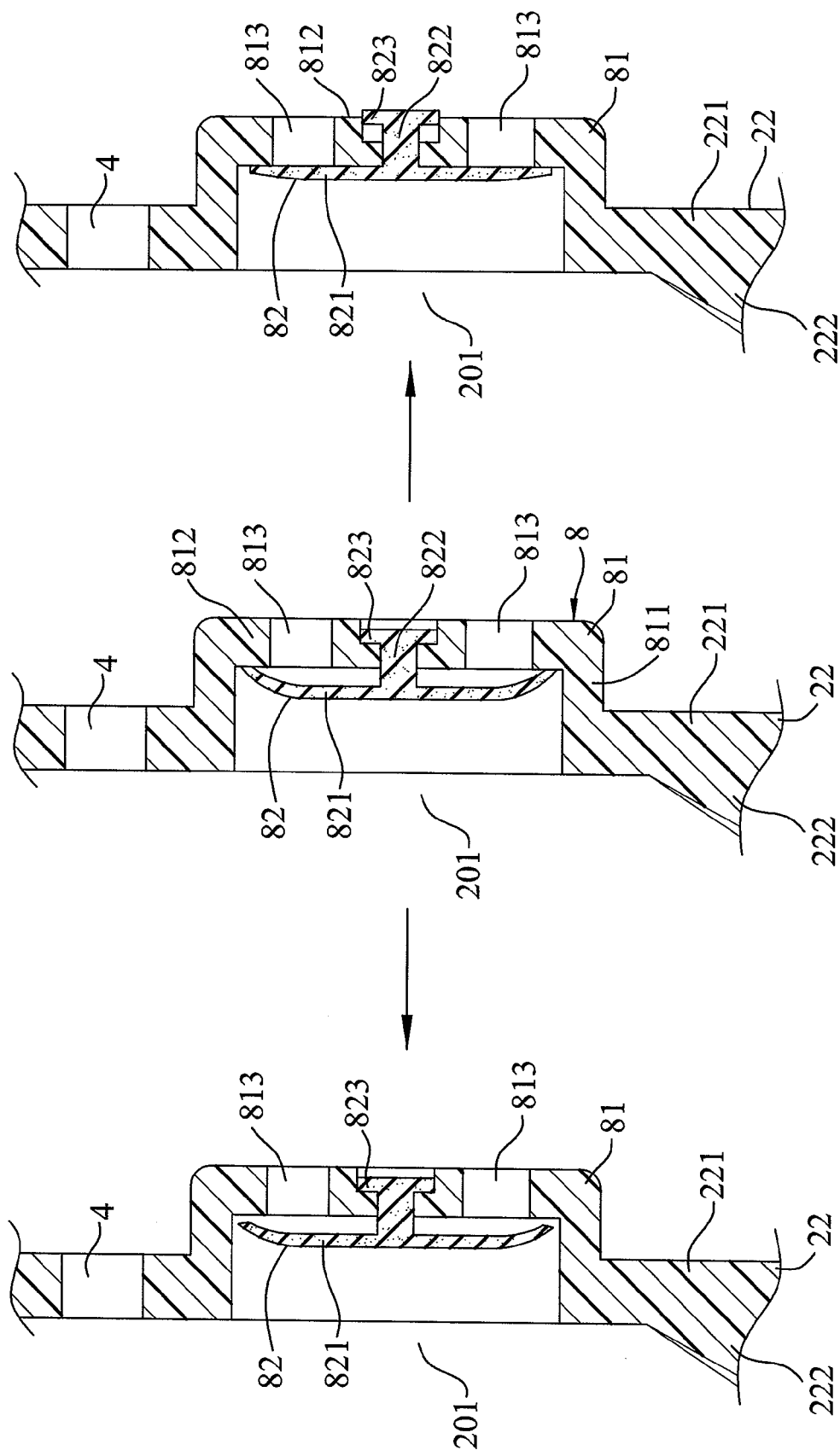
FIG. 12 is a sectional diagram illustrating operation of a valve of the fourth preferred embodiment.

Referring to FIGS. 10 to 12, differences between the first and fourth preferred embodiments reside in the structural configurations of the tube 2, the remote controller 6 and the sound generator 7, and the speech aid system further includes a valve 8.

In the fourth preferred embodiment, the connecting section 21 and the artificial glottis section 22 are separable from each other, and the tube 2 further includes a filter component 23 disposed between the connecting section 21 and the tubular portion 221 of the artificial glottis section 22. In this embodiment, the connecting portion 21 is L-shaped, and is threadedly engaged with the artificial glottis section 22. The artificial glottis section 22 further has an extending tubular portion 224 protruding from the outer peripheral surface of the tubular portion 221. The internal spaces of the extending tubular portion 224 and the tubular portion 221 are spatially communicated with each other. In this embodiment, the tubular portion 221 only has the first space 201, and the extending tubular portion 224 has the breathing hole 220 formed in a wall thereof.

It should be noted that connection between the connecting section 21 and the tubular portion 221 should not be limited to threaded engagement, and may be snap engagement, etc.

The filter component 23 is configured to prevent particles from entering the connecting section 21 via the tubular portion 221, so as to achieve the blocking effect of nasal hairs and nasal mucosa during breathing. The filter component 23 may be replaced by separating the connecting section 21 and the artificial glottis section 22 from each other. The gate 3 is mounted to the extending tubular portion 224 and is operable to open and close the breathing hole 220.

The valve 8 includes a hollow installation base 81 that is fixedly connected to the outer peripheral surface of the tubular portion 221, and that has an internal space in spatial communication with the internal space of the tubular portion 221, and a valve piece 82 installed in the installation base 81. The installation base 81 has a ring portion 811 protruding from the outer peripheral surface of the tubular portion 221, and an end wall portion 812 disposed at an end of the ring portion 811 distal from the outer peripheral surface of the tubular portion 221. The end wall portion 812 is formed with a plurality of through holes 813 extending therethrough in an axial direction of the ring portion 811.

The valve piece 82 is made of an elastically deformable material (e.g., silicone, rubber, etc.), and has a plate portion 821 that is coaxially disposed within the ring portion 811 and that is elastically deformable to seal the through holes 813, an extension portion 822 that extends coaxially from the plate portion 821 into the end wall portion 812 and that is movable in a direction parallel to a longitudinal axis of the ring portion 811, and a limiting portion 823 that extends radially and outwardly from an end of the extension portion 822 distal from the plate portion 821 and that is disposed to abut against one side of the end wall portion 812 opposite to the plate portion 821.

The plate portion 821 has an outer diameter smaller than an inner diameter of the ring portion 811, and a periphery disposed to elastically abut against an inner-side surface of the end wall portion 812. The plate portion 821 is configured to be elastically deformed by a relatively positive air pressure resulting from airflow in the tubular portion 221 (e.g., airflow exhaled by the user 900), resulting in sealing abutment against the inner-side surface of the end wall portion 812, so as to seal the through holes 813. The plate portion 821 is further configured to be elastically deformed toward an interior of the tubular portion 221 by a relatively negative air pressure in the first space 201, or by a relatively positive air pressure resulting from airflow outside of the through holes 813, and to depart from the inner-side surface of the end wall portion 812, so that ambient air may enter the first space 201. For example, the plate portion 821 may be deformed due to the negative air pressure in the first space 201, which results from inhaling by the user 900. In other words, the valve 8 may be opened and closed in turns in response to the breathing of the user 900.

Through such a configuration, the tube 2, the gate 3, and the valve 8 may cooperate together to simulate the physical function of an ordinary person's larynx during breathing and speaking. Further details will be described as follows.

When the gate 3 is controlled to open the breathing hole 220, the user 900 may breathe normally, achieving the physical larynx function of an ordinary person when breathing.

When the user 900 attempts to speak, the gate 3 is controlled to close the breathing hole 220 such that the speech aid system has a configuration similar to that of a larynx of an ordinary person when speaking. When the user 900 starts speaking, airflow applied by the user 900 to the tube 2 results in a relatively positive air pressure to close the valve 8, such that the air exhaled during speech is compressed to flow through the artificial glottis 20, and the voice parameter acquiring device 4 generates the voice parameter signal accordingly. When the user 900 finishes speaking a sentence or phrase and inhales, the valve 8 is opened such that ambient air is able to enter the lungs through the tube 2 for proceeding with the next speech. The physical function of a larynx of an ordinary person may thus be simulated during continuous speech without continuous operation of the remote controller 6. Operation of the remote controller 6 is thus required only when the user 900 no longer attempts to speak for controlling the gate 3 to open, such that the user 900 may breathe normally through the breathing hole 220. Through such a design, the user 900 may easily get used to operations of the speech aid system according to this invention without particularly changing the ordinary mouth shape and the ordinary breathing manner when speaking.

In addition, by virtue of the valve 8, when the gate 3 is closed and is unable to be opened, for example, due to malfunction of the gate 3 or low battery of the remote controller 6, the user 900 may still breathe and speak via the valve 8, thereby enhancing safety of the speech aid system of the present invention.

In this embodiment, the voice parameter acquiring device 4 and the processor 5 are mounted to the tubular portion 221, and the voice parameter acquiring device 4 has a sensing portion configured to sense a difference between air pressure in the first space 201 and the ambient air pressure.

In this embodiment, the remote controller 6 does not have the audio frequency modulating unit, and instead has a warning light unit 66 electrically coupled to the gate control unit 62. The warning light unit 66 is configured to emit light when the control button 621 is pressed for generation of the gate closing signal, so as to warn the user 900 that the breathing hole 220 is closed. In addition, the warning light unit 66 stops light emission when the gate control unit 62 generates the gate opening signal.

The sound generator 7 includes a plate-shaped base 73 configured for mounting to a hard palate in the oral cavity 902 of the user 900, and a sound producing unit 72 and a wireless receiver unit 71 that are disposed within the base 73. The sound producing unit 72 includes a resonant pipe 721 that extends in the base 73, and an electroacoustic module 724 operable to produce the substitute glottal sound in response to the audio signal received by the wireless receiver unit 71. The resonant pipe 721 has a sound output end 722 that protrudes and is exposed from a rear part of a bottom surface of the base 73 and that slantingly faces downward and toward a mouth opening of the user 900, and a sound inlet end 723. The electroacoustic module 724 is mounted to the sound inlet end 723, and is configured to output the substitute glottal sound into the resonant pipe 721, such that the substitute glottal sound is transmitted into the oral cavity 902 via the sound output end 722 after resonating and forming formants in the resonant pipe 721. Through the design of the resonant pipe 721, generation of the formants resulting from resonance of the glottal sound in the gullet and the oral cavity during speech by an ordinary person may be simulated, such that the user 900 may articulate the substitute glottal sound into desired spoken sound with ordinary breathing and the ordinary mouth shape. In addition, a desired tone may be obtained through a length design of the resonant pipe 721, which determines a frequency of the formants. In practice, the length of the resonant pipe 721 may be designed according to the sex, the age, and the preference of the user 900, so as to obtain a desired tone, resulting in promotion of functionality of the speech aid system.

To sum up, through the structural design of the tube 2 that simulates the glottis structure of an ordinary person during speaking, the air that is compressed to flow through the artificial glottis 20 during speaking may be similar to the air flowing through the glottis of an ordinary person. Then, according to the voice parameter signal thus produced, the processor 5 generates the audio signal that is similar to the sound wave produced by the human glottis, and the sound generator 7 receives the audio signal and produces the substitute glottal sound accordingly in the oral cavity 902. In addition, the time elapsed between obtaining the voice parameter signal and producing the substitute glottal sound is so short to be similar to the time elapsed when air from the lungs flows through the glottis to vibrate the vocal cord to produce the glottal sound, so that the sound generator 7 may produce the substitute glottal sound just at the time that the user 900 configures the mouth shape. Therefore, the user 900 may speak correctly with volume variation and clear pauses, and the tone of the substitute glottal sound may be adjusted by operation of the remote controller 6, so that the user 900 may speak like an ordinary person, and the drawback of the aforementioned conventional artificial larynx may be alleviated.

Moreover, by virtue of the filter component 23 that may effectively prevent particles from entering the connecting section 21 via the breathing hole 220, the user's health may be ensured, and the separable design of the connecting section 21 and the artificial glottis section 22 facilitates cleaning of the tube 2. Furthermore, when the gate 3 is unable to be opened, the user 900 may still breathe and speak through the valve 8, thus ensuring safety when using the tube 2.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A speech aid system comprising:
    a tube configured for mounting at a tracheostomy of a user;
    a voice parameter acquiring device mounted to said tube, and configured to sense airflow applied within said tube resulting from attempt by the user to speak, and to generate a voice parameter signal according to the airflow sensed thereby;
    a processor configured to receive the voice parameter signal from said voice parameter acquiring device, and to generate an audio signal corresponding to the voice parameter signal; and
    a sound generator configured for mounting in an oral cavity of the user, configured to receive the audio signal from said processor, and configured to produce a substitute glottal sound corresponding to the audio signal.

2. The speech aid system as claimed in claim 1, wherein said tube has at least one protrusion that protrudes radially and inwardly from an inner peripheral surface of said tube and that is configured to form an artificial glottis extending along an axial direction of said tube.

3. The speech aid system as claimed in claim 2, wherein said tube has a first space and a second space formed therein at opposite sides of said artificial glottis within said tube, said first space to be in spatial communication with the tracheostomy, said artificial glottis having a radial size that is gradually reduced in a direction from said first space to said second space.

4. The speech aid system as claimed in claim 2, wherein said tube has a first space formed therein at a side of said artificial glottis, said first space to be in spatial communication with the tracheostomy, said artificial glottis to be in spatial communication with external environment, and having a radial size that is gradually reduced in a direction from said first space to the external environment.

5. The speech aid system as claimed in claim 2, wherein said tube has two of said protrusions that protrude toward each other, that are spaced apart from each other, and that are configured to form said artificial glottis therebetween.

6. The speech aid system as claimed in claim 2, wherein said tube has a connecting section configured for mounting at the tracheostomy of the user, and an artificial glottis section connected to said connecting section and having said at least one protrusion.

7. The speech aid system as claimed in claim 6, wherein said tube includes a filter component disposed between said connecting section and said artificial glottis section, and configured to prevent particles from entering said connecting section via said artificial glottis section.

8. The speech aid system as claimed in claim 6, further comprising a valve connected to an outer peripheral surface of said artificial glottis section, and configured to be closed by positive air pressure within said artificial glottis section, and to be opened by negative air pressure within said artificial glottis section for allowing ambient air to enter said artificial glottis section via said valve.

9. The speech aid system as claimed in claim 8, wherein:
    said valve includes a hollow installation base that is fixedly connected to said outer peripheral surface of said artificial glottis section, and that has an internal space in spatial communication with an internal space of said artificial glottis section, and a valve piece that is elastically deformable and that is installed in said installation base;
    said installation base has a ring portion protruding from said outer peripheral surface of said artificial glottis section, and an end wall portion disposed at an end of said ring portion distal from said outer peripheral surface of said artificial glottis section;
    said end wall portion is formed with at least one through hole therethrough; and
    said valve piece has a plate portion that is disposed within said ring portion and that is elastically deformable to seal said through hole, an extension portion that extends from said plate portion into said end wall portion and that is movable in a direction parallel to a longitudinal axis of said ring portion, and a limiting portion that extends radially and outwardly from an end of said extension portion distal from said plate portion and that is disposed to abut against one side of said end wall portion opposite to said plate portion.

10. The speech aid system as claimed in claim 6, wherein said connecting section and said artificial glottis section are separable.

11. The speech aid system as claimed in claim 1, wherein said tube is formed with a breathing hole extending through a tube wall thereof, said speech aid system further comprising:
   a gate mounted to said tube and operable to open and close said breathing hole; and
   a remote controller operatively associated with said gate to control opening and closing actions of said gate.

12. The speech aid system as claimed in claim 11, wherein said remote controller includes a gate control unit operable to generate a gate control signal, and a wireless transmission unit electrically connected to said gate control unit and configured to wirelessly transmit the gate control signal; and
   said processor is disposed at said tube, is electrically connected to said gate, and includes:
   a wireless transceiver unit that is configured to wirelessly receive the gate control signal, and to wirelessly transmit the audio signal for reception by said sound generator,
   a signal processing unit that is electrically connected to said voice parameter acquiring unit, and that is configured to generate the audio signal, and
   a control unit that is configured to control opening and closing actions of said gate in response to the gate control signal received by said wireless transceiver unit.

13. The speech aid system as claimed in claim 12, wherein said gate control unit is configured to continuously generate the gate control signal such that said control unit controls said gate to close said breathing hole only when being operated, and said control unit controls said gate to open said breathing hole when said wireless transceiver unit does not receive the gate control signal.

14. The speech aid system as claimed in claim 12, wherein said gate control unit is configured to generate the gate control signal such that said control unit controls said gate to close and open said breathing hole in turns during repeated operation of said gate control unit.

15. The speech aid system as claimed in claim 12, wherein said remote controller further includes a warning light unit configured to emit light when said gate control unit generates said gate control signal to which said control unit responds by controlling closing action of said gate.

16. The speech aid system as claimed in claim 12, wherein said remote controller includes a ring to be worn by the user, said gate control unit being installed on and exposed from said ring.

17. The speech aid system as claimed in claim 1, further comprising a remote controller including an audio frequency modulating unit that is operable to generate a frequency modulation signal, and a wireless transmission unit that is configured to wirelessly transmit the frequency modulation signal,
   wherein said processor includes a wireless transceiver unit configured to wirelessly receive the frequency modulation signal, and a signal processing unit configured to modulate an audio frequency parameter of the audio signal according to the frequency modulation signal received by said wireless transceiver unit, said wireless transceiver unit being further configured to transmit to said sound generator the audio signal having the modulated audio frequency parameter.

18. The speech aid system as claimed in claim 1, wherein said sound generator includes:
   a wireless receiver unit configured to wirelessly receive the audio signal from said processor; and
   a sound producing unit electrically connected to said wireless receiver unit, and including an electroacoustic module operable to produce the substitute glottal sound in response to the audio signal received by said wireless receiver unit.

19. The speech aid system as claimed in claim 18, wherein said sound producing unit has a sound output surface extending horizontally and facing a mouth opening of the user.

20. The speech aid system as claimed in claim 18, wherein:
   said sound generator further includes a base within which said sound producing unit is disposed, said base being configured for mounting in the oral cavity of the user; and
   said sound producing unit further includes a resonant pipe that is configured to allow the substitute glottal sound to resonate therein, and that has a sound output end exposed from a surface of said base that faces toward a mouth opening of the user.

21. The speech aid system as claimed in claim 2, wherein said voice parameter acquiring device is an air flow meter that is mounted to said protrusion and that generates the voice parameter signal according to speed of airflow passing through said artificial glottis.

22. The speech aid system as claimed in claim 3, wherein said voice parameter acquiring device is an acoustoelectric transducer that is mounted in said second space and that generates the voice parameter signal according to amplitude of a pressure wave generated by passage of airflow through said artificial glottis.

23. The speech aid system as claimed in claim 3, wherein said voice parameter acquiring device is a pressure sensor that generates the voice parameter signal according to a difference between air pressure in the first space and ambient air pressure.

24. The speech aid system as claimed in claim 4, wherein said voice parameter acquiring device is a pressure sensor that generates the voice parameter signal according to a difference between air pressure in the first space and ambient air pressure.

* * * * *